United States Patent
Lee

(10) Patent No.: US 11,970,691 B2
(45) Date of Patent: Apr. 30, 2024

(54) IMMOBILIZED THERMOSTABLE TREHALOSE SYNTHASE AND METHOD FOR PRODUCING TREHALOSE AND TREHALULOSE BY USING SAME

(71) Applicant: National Taiwan Normal University, Taipei (TW)

(72) Inventor: Guan-Chiun Lee, Taipei (TW)

(73) Assignee: National Taiwan Normal University, Taipei (TW)

( * ) Notice: Subject to any disclaimer, the term of this patent is extended or adjusted under 35 U.S.C. 154(b) by 140 days.

(21) Appl. No.: 17/206,944

(22) Filed: Mar. 19, 2021

(65) Prior Publication Data
US 2022/0186204 A1 Jun. 16, 2022

(30) Foreign Application Priority Data

Dec. 11, 2020 (TW) ................ 109143883

(51) Int. Cl.
 C12N 11/12 (2006.01)
 C12N 9/90 (2006.01)
 C12P 19/12 (2006.01)

(52) U.S. Cl.
 CPC ........... *C12N 11/12* (2013.01); *C12N 9/90* (2013.01); *C12P 19/12* (2013.01); *C12Y 504/99016* (2013.01)

(58) Field of Classification Search
 CPC .................................................. C07K 2319/20
 See application file for complete search history.

(56) References Cited

PUBLICATIONS

Wang ("Role of the C-Terminal Domain of Thermus Thermophilus Trehalose Synthase in the Thermophilicity, Thermostability and Efficient Production of Trehalose" Journal of Agricultural and Food Chemistry, 2007, 55, 3435-3443 (Year: 2007).*
Ong ("Enzyme Immobilization using the Cellulose-Binding Domain of a Cellulomonas Fimi Exoglucanse", Biotechnology, vol. 7 1989 , 604-607 (Year: 1989).*
O'Neill ("Overproduction from a Cellulase Gene with a High Guanosine-Plus-Cytosine Content in *Escherichia coli*", Applied and Environmental Microbiology, 1986, 737-743), (Year: 1986).*
Whittle ("Molecular Cloning of a Cellulomonas fimi cellulase gene in *Escherichia coli*" Gene, 17 (1982), 139-145). (Year: 1982).*
Of Ong-2 (The Cellulose-Binding Domain (CBDcex) of an Exoglucanase from Cellulomonase fimi: Production in *Escherichia coli* and Characterization of the Polypeptide Biotechnology and Bioengineering vol. 42. (1993) 401-409). (Year: 1993).*
NCBI ("endo-1,4-beta-xylanase [Cellulomonas fimi]", Ncbi, NCBI Reference Sequence: WP_041553359.1, from https://www.ncbi.nlm.nih.gov/protein/WP_041553359.1?report=genbank&log$=protalign&blast_rank=1&RID=CW63RP5Y016, accessed on Aug. 5, 2023 (Year: 2023).*
Alhaeri ("Engineering and Production of Glucooligosaccharide Oxidases for Site-Specific Activation of Cellulose and Hemicellulose Substrates", PH.D. Department of Chemical Engineering and Applied Chemistry, University of Toronto, Toronto Ontario Canada, 2015)) (Year: 2015).*
Ouyang et al., "Advances in cellulose-binding module," Chinese Journal of Bioprocess Engineering, Mar. 2008, vol. 6, No. 2, pp. 10-16 (English Abstract).
Wei et al., "Simple, fast, and efficient process for producing and purifying trehalulose," Food Chemistry, 2013, vol. 138, pp. 1183-1188.

* cited by examiner

*Primary Examiner* — Robert J Yamasaki
*Assistant Examiner* — Charles Zoltan Constantine
(74) *Attorney, Agent, or Firm* — Melissa Hunter-Ensor; Leslie Serunian; Greenberg Traurig, LLP

(57) ABSTRACT

Provided is an immobilized thermostable trehalose synthase including an amino acid sequence of a trehalose synthase domain and an amino acid sequence of a cellulose binding domain. Also provided is a method for converting maltose into trehalose or for converting sucrose into trehalulose by using the immobilized thermostable trehalose synthase.

15 Claims, 4 Drawing Sheets

Specification includes a Sequence Listing.

SEQUENCE LISTING

```
<160> NUMBER OF SEQ ID NOS: 6

<210> SEQ ID NO 1
<211> LENGTH: 965
<212> TYPE: PRT
<213> ORGANISM: Thermus thermophilus
<300> PUBLICATION INFORMATION:
<308> DATABASE ACCESSION NUMBER: NCBI/WP_024119343
<309> DATABASE ENTRY DATE: 2014-01-03
<313> RELEVANT RESIDUES IN SEQ ID NO: (1)..(965)

<400> SEQUENCE: 1

Met Asp Pro Leu Trp Tyr Lys Asp Ala Val Ile Tyr Gln Leu His Val
1               5                   10                  15

Arg Ser Phe Phe Asp Ala Asn Asn Asp Gly Tyr Gly Asp Phe Glu Gly
            20                  25                  30
```

```
Leu Arg Arg Lys Leu Pro Tyr Leu Glu Glu Leu Gly Val Asn Thr Leu
        35                  40                  45
Trp Leu Met Pro Phe Phe Gln Ser Pro Leu Arg Asp Asp Gly Tyr Asp
     50                  55                  60
Ile Ser Asp Tyr Tyr Gln Ile Leu Pro Val His Gly Thr Leu Glu Asp
 65                  70                  75                  80
Phe Lys Arg Phe Leu Asp Glu Ala His Gly Arg Gly Met Lys Val Ile
                 85                  90                  95
Ile Glu Leu Val Leu Asn His Thr Ser Ile Asp His Pro Trp Phe Gln
                100                 105                 110
Glu Ala Arg Lys Pro Asn Ser Pro Met Arg Asp Trp Tyr Val Trp Ser
            115                 120                 125
Asp Thr Pro Glu Lys Tyr Lys Gly Val Arg Val Ile Phe Lys Asp Phe
        130                 135                 140
Glu Thr Ser Asn Trp Thr Phe Asp Pro Val Ala Lys Ala Tyr Tyr Trp
145                 150                 155                 160
His Arg Phe Tyr Trp His Gln Pro Asp Leu Asn Trp Asp Asn Pro Glu
                165                 170                 175
Val Glu Lys Ala Ile His Gln Val Met Phe Phe Trp Ala Asp Leu Gly
            180                 185                 190
Val Asp Gly Phe Arg Leu Asp Ala Ile Pro Tyr Leu Tyr Glu Arg Glu
        195                 200                 205
Gly Thr Ser Cys Glu Asn Leu Pro Glu Thr Ile Glu Ala Val Lys Arg
    210                 215                 220
Leu Arg Lys Ala Leu Glu Arg Tyr Gly Pro Gly Lys Ile Leu Leu
225                 230                 235                 240
Ala Glu Ala Asn Met Trp Pro Glu Glu Thr Leu Pro Tyr Phe Gly Asp
                245                 250                 255
Gly Asp Gly Val His Met Ala Tyr Asn Phe Pro Leu Met Pro Arg Ile
            260                 265                 270
Phe Met Ala Leu Lys Arg Glu Asp Arg Gly Pro Ile Glu Thr Met Leu
        275                 280                 285
Lys Glu Thr Glu Gly Ile Pro Glu Thr Ala Gln Trp Ala Leu Phe Leu
    290                 295                 300
Arg Asn His Asp Glu Leu Thr Leu Glu Lys Val Thr Glu Glu Glu Arg
305                 310                 315                 320
Glu Phe Met Tyr Glu Ala Tyr Ala Pro Asp Pro Lys Phe Arg Ile Asn
                325                 330                 335
Leu Gly Ile Arg Arg Arg Leu Met Pro Leu Leu Gly Gly Asp Arg Arg
            340                 345                 350
Arg Tyr Glu Leu Leu Thr Ala Leu Leu Leu Thr Leu Lys Gly Thr Pro
        355                 360                 365
Ile Val Tyr Tyr Gly Asp Glu Ile Gly Met Gly Asp Asn Pro Phe Leu
    370                 375                 380
Gly Asp Arg Asn Gly Val Arg Thr Pro Met Gln Trp Ser Gln Asp Arg
385                 390                 395                 400
Asn Ala Gly Phe Ser Arg Ala Pro Tyr His Ala Leu Phe Leu Pro Pro
                405                 410                 415
Val Ser Glu Gly Pro Tyr Ser Tyr His Phe Val Asn Val Glu Ala Gln
            420                 425                 430
Arg Glu Asn Pro His Ser Leu Leu Ser Phe Asn Arg Arg Phe Leu Ala
        435                 440                 445
```

-continued

Leu Arg Asn Gln His Ala Lys Ile Phe Gly Arg Gly Ser Leu Thr Leu
450                     455                 460

Leu Pro Val Glu Asn Arg Arg Val Leu Ala Tyr Leu Arg Glu His Glu
465                 470                 475                 480

Gly Glu Arg Val Leu Val Val Ala Asn Leu Ser Arg Tyr Thr Gln Ala
                485                 490                 495

Phe Asp Leu Pro Leu Glu Ala Tyr Gln Gly Leu Val Pro Val Glu Leu
            500                 505                 510

Phe Ser Gln Gln Pro Phe Pro Val Glu Gly Arg Tyr Arg Leu Thr
        515                 520                 525

Leu Gly Pro His Gly Phe Ala Leu Phe Ala Leu Lys Pro Val Glu Ala
530                 535                 540

Val Leu His Leu Pro Ser Pro Asp Trp Ala Glu Pro Ala Pro Glu
545                 550                 555                 560

Glu Ala Asp Leu Pro Arg Val His Met Pro Gly Pro Glu Val Leu
                565                 570                 575

Leu Val Asp Thr Leu Val His Glu Arg Gly Arg Glu Leu Leu Asn
            580                 585                 590

Ala Leu Ala Gln Thr Leu Lys Glu Lys Ser Trp Leu Ala Leu Lys Pro
595                 600                 605

Gln Lys Val Ala Leu Leu Asp Ala Leu Arg Phe Gln Lys Asp Pro Pro
610                 615                 620

Leu Tyr Leu Thr Leu Leu Gln Leu Glu Asn His Arg Thr Leu Gln Val
625                 630                 635                 640

Phe Leu Pro Leu Leu Trp Ser Pro Gln Arg Arg Glu Gly Pro Gly Leu
                645                 650                 655

Phe Ala Arg Thr His Gly Gln Pro Gly Tyr Phe Tyr Glu Leu Ser Leu
                660                 665                 670

Asp Pro Gly Phe Tyr Arg Leu Leu Ala Arg Leu Lys Glu Gly Phe
            675                 680                 685

Glu Gly Arg Ser Leu Arg Ala Tyr Tyr Arg Gly Arg His Pro Gly Pro
690                 695                 700

Val Pro Glu Ala Val Asp Leu Leu Arg Pro Gly Leu Ala Ala Gly Glu
705                 710                 715                 720

Gly Val Trp Val Gln Leu Gly Leu Val Gln Asp Gly Gly Leu Asp Arg
                725                 730                 735

Thr Glu Arg Val Leu Pro Arg Leu Asp Leu Pro Trp Val Leu Arg Pro
                740                 745                 750

Glu Gly Gly Leu Phe Trp Glu Arg Gly Ala Ser Arg Arg Val Leu Ala
                755                 760                 765

Leu Thr Gly Ser Leu Pro Pro Gly Arg Pro Gln Asp Leu Phe Ala Ala
770                 775                 780

Leu Glu Val Arg Leu Leu Glu Ser Leu Pro Arg Leu Arg Gly His Ala
785                 790                 795                 800

Pro Gly Thr Pro Gly Leu Leu Pro Gly Ala Leu His Glu Thr Glu Ala
                805                 810                 815

Leu Val Arg Leu Leu Gly Val Arg Leu Ala Leu Leu His Arg Ala Leu
                820                 825                 830

Gly Glu Val Glu Gly Val Gly Gly His Pro Leu Leu Gly Arg Gly
                835                 840                 845

Leu Gly Ala Phe Leu Glu Leu Glu Gly Glu Val Tyr Leu Val Ala Leu
850                 855                 860

Gly Ala Glu Lys Arg Gly Thr Val Glu Glu Asp Leu Ala Arg Leu Ala

```
                  865                 870                 875                 880

Tyr Asp Val Glu Arg Ala Val His Leu Ala Leu Glu Ala Leu Glu Ala
                            885                 890                 895

Glu Leu Trp Ala Phe Ala Glu Glu Val Ala Asp His Leu His Ala Ala
                900                 905                 910

Phe Leu Gln Ala Tyr Arg Ser Ala Leu Pro Glu Glu Ala Leu Glu Glu
                915                 920                 925

Ala Gly Trp Thr Arg His Met Ala Glu Val Ala Ala Glu His Leu His
                930                 935                 940

Arg Glu Glu Arg Pro Ala Arg Lys Arg Ile His Glu Arg Trp Gln Ala
945                 950                 955                 960

Lys Ala Gly Lys Ala
                965

<210> SEQ ID NO 2
<211> LENGTH: 114
<212> TYPE: PRT
<213> ORGANISM: Cellulomonas fimi
<300> PUBLICATION INFORMATION:
<308> DATABASE ACCESSION NUMBER: NCBI/AAA56791
<309> DATABASE ENTRY DATE: 1994-12-01
<313> RELEVANT RESIDUES IN SEQ ID NO: (371)..(484)

<400> SEQUENCE: 2

Pro Thr Pro Thr Pro Thr Ser Gly Pro Ala Gly Cys Gln Val Leu Trp
1               5                   10                  15

Gly Val Asn Gln Trp Asn Thr Gly Phe Thr Ala Asn Val Thr Val Lys
                20                  25                  30

Asn Thr Ser Ser Ala Pro Val Asp Gly Trp Thr Leu Thr Phe Ser Phe
            35                  40                  45

Pro Ser Gly Gln Gln Val Thr Gln Ala Trp Ser Ser Thr Val Thr Gln
    50                  55                  60

Ser Gly Ser Ala Val Thr Val Arg Asn Ala Pro Trp Asn Gly Ser Ile
65                  70                  75                  80

Pro Ala Gly Gly Thr Ala Gln Phe Gly Phe Asn Gly Ser His Thr Gly
                85                  90                  95

Thr Asn Ala Ala Pro Thr Ala Phe Ser Leu Asn Gly Thr Pro Cys Thr
                100                 105                 110

Val Gly

<210> SEQ ID NO 3
<211> LENGTH: 1079
<212> TYPE: PRT
<213> ORGANISM: Artificial Sequence
<220> FEATURE:
<223> OTHER INFORMATION: TrTS-CBD recombinant protein

<400> SEQUENCE: 3

Met Asp Pro Leu Trp Tyr Lys Asp Ala Val Ile Tyr Gln Leu His Val
1               5                   10                  15

Arg Ser Phe Phe Asp Ala Asn Asn Asp Gly Tyr Gly Asp Phe Glu Gly
                20                  25                  30

Leu Arg Arg Lys Leu Pro Tyr Leu Glu Glu Leu Gly Val Asn Thr Leu
            35                  40                  45

Trp Leu Met Pro Phe Phe Gln Ser Pro Leu Arg Asp Asp Gly Tyr Asp
    50                  55                  60

Ile Ser Asp Tyr Tyr Gln Ile Leu Pro Val His Gly Thr Leu Glu Asp
65                  70                  75                  80
```

```
Phe Lys Arg Phe Leu Asp Glu Ala His Gly Arg Gly Met Lys Val Ile
                 85                  90                  95

Ile Glu Leu Val Leu Asn His Thr Ser Ile Asp His Pro Trp Phe Gln
                100                 105                 110

Glu Ala Arg Lys Pro Asn Ser Pro Met Arg Asp Trp Tyr Val Trp Ser
                115                 120                 125

Asp Thr Pro Glu Lys Tyr Lys Gly Val Arg Val Ile Phe Lys Asp Phe
            130                 135                 140

Glu Thr Ser Asn Trp Thr Phe Asp Pro Val Ala Lys Ala Tyr Tyr Trp
145                 150                 155                 160

His Arg Phe Tyr Trp His Gln Pro Asp Leu Asn Trp Asp Asn Pro Glu
                165                 170                 175

Val Glu Lys Ala Ile His Gln Val Met Phe Phe Trp Ala Asp Leu Gly
                180                 185                 190

Val Asp Gly Phe Arg Leu Asp Ala Ile Pro Tyr Leu Tyr Glu Arg Glu
                195                 200                 205

Gly Thr Ser Cys Glu Asn Leu Pro Glu Thr Ile Glu Ala Val Lys Arg
            210                 215                 220

Leu Arg Lys Ala Leu Glu Glu Arg Tyr Gly Pro Gly Lys Ile Leu Leu
225                 230                 235                 240

Ala Glu Ala Asn Met Trp Pro Glu Glu Thr Leu Pro Tyr Phe Gly Asp
                245                 250                 255

Gly Asp Gly Val His Met Ala Tyr Asn Phe Pro Leu Met Pro Arg Ile
                260                 265                 270

Phe Met Ala Leu Lys Arg Glu Asp Arg Gly Pro Ile Glu Thr Met Leu
                275                 280                 285

Lys Glu Thr Glu Gly Ile Pro Glu Thr Ala Gln Trp Ala Leu Phe Leu
            290                 295                 300

Arg Asn His Asp Glu Leu Thr Leu Glu Lys Val Thr Glu Glu Glu Arg
305                 310                 315                 320

Glu Phe Met Tyr Glu Ala Tyr Ala Pro Asp Pro Lys Phe Arg Ile Asn
                325                 330                 335

Leu Gly Ile Arg Arg Arg Leu Met Pro Leu Leu Gly Gly Asp Arg Arg
                340                 345                 350

Arg Tyr Glu Leu Leu Thr Ala Leu Leu Leu Thr Leu Lys Gly Thr Pro
            355                 360                 365

Ile Val Tyr Tyr Gly Asp Glu Ile Gly Met Gly Asp Asn Pro Phe Leu
            370                 375                 380

Gly Asp Arg Asn Gly Val Arg Thr Pro Met Gln Trp Ser Gln Asp Arg
385                 390                 395                 400

Asn Ala Gly Phe Ser Arg Ala Pro Tyr His Ala Leu Phe Leu Pro Pro
                405                 410                 415

Val Ser Glu Gly Pro Tyr Ser Tyr His Phe Val Asn Val Glu Ala Gln
                420                 425                 430

Arg Glu Asn Pro His Ser Leu Leu Ser Phe Asn Arg Phe Leu Ala
            435                 440                 445

Leu Arg Asn Gln His Ala Lys Ile Phe Gly Arg Gly Ser Leu Thr Leu
450                 455                 460

Leu Pro Val Glu Asn Arg Arg Val Leu Ala Tyr Leu Arg Glu His Glu
465                 470                 475                 480

Gly Glu Arg Val Leu Val Val Ala Asn Leu Ser Arg Tyr Thr Gln Ala
                485                 490                 495
```

```
Phe Asp Leu Pro Leu Glu Ala Tyr Gln Gly Leu Val Pro Val Glu Leu
                500                 505                 510
Phe Ser Gln Gln Pro Phe Pro Val Glu Gly Arg Tyr Arg Leu Thr
        515                 520                 525
Leu Gly Pro His Gly Phe Ala Leu Phe Ala Leu Lys Pro Val Glu Ala
        530                 535                 540
Val Leu His Leu Pro Ser Pro Asp Trp Ala Glu Pro Ala Pro Glu
545                 550                 555                 560
Glu Ala Asp Leu Pro Arg Val His Met Pro Gly Gly Pro Glu Val Leu
                565                 570                 575
Leu Val Asp Thr Leu Val His Glu Arg Gly Arg Glu Leu Leu Asn
        580                 585                 590
Ala Leu Ala Gln Thr Leu Lys Glu Lys Ser Trp Leu Ala Leu Lys Pro
        595                 600                 605
Gln Lys Val Ala Leu Leu Asp Ala Leu Arg Phe Gln Lys Asp Pro Pro
        610                 615                 620
Leu Tyr Leu Thr Leu Leu Gln Leu Glu Asn His Arg Thr Leu Gln Val
625                 630                 635                 640
Phe Leu Pro Leu Leu Trp Ser Pro Gln Arg Arg Glu Gly Pro Gly Leu
                645                 650                 655
Phe Ala Arg Thr His Gly Gln Pro Gly Tyr Phe Tyr Glu Leu Ser Leu
                660                 665                 670
Asp Pro Gly Phe Tyr Arg Leu Leu Ala Arg Leu Lys Glu Gly Phe
        675                 680                 685
Glu Gly Arg Ser Leu Arg Ala Tyr Tyr Arg Gly Arg His Pro Gly Pro
        690                 695                 700
Val Pro Glu Ala Val Asp Leu Leu Arg Pro Gly Leu Ala Ala Gly Glu
705                 710                 715                 720
Gly Val Trp Val Gln Leu Gly Leu Val Gln Asp Gly Gly Leu Asp Arg
                725                 730                 735
Thr Glu Arg Val Leu Pro Arg Leu Asp Leu Pro Trp Val Leu Arg Pro
                740                 745                 750
Glu Gly Gly Leu Phe Trp Glu Arg Gly Ala Ser Arg Arg Val Leu Ala
        755                 760                 765
Leu Thr Gly Ser Leu Pro Pro Gly Arg Pro Gln Asp Leu Phe Ala Ala
        770                 775                 780
Leu Glu Val Arg Leu Leu Glu Ser Leu Pro Arg Leu Arg Gly His Ala
785                 790                 795                 800
Pro Gly Thr Pro Gly Leu Leu Pro Gly Ala Leu His Glu Thr Glu Ala
                805                 810                 815
Leu Val Arg Leu Leu Gly Val Arg Leu Ala Leu Leu His Arg Ala Leu
                820                 825                 830
Gly Glu Val Glu Gly Val Val Gly Gly His Pro Leu Leu Gly Arg Gly
        835                 840                 845
Leu Gly Ala Phe Leu Glu Leu Glu Gly Glu Val Tyr Leu Val Ala Leu
        850                 855                 860
Gly Ala Glu Lys Arg Gly Thr Val Glu Glu Asp Leu Ala Arg Leu Ala
865                 870                 875                 880
Tyr Asp Val Glu Arg Ala Val His Leu Ala Leu Glu Ala Leu Glu Ala
                885                 890                 895
Glu Leu Trp Ala Phe Ala Glu Glu Val Ala Asp His Leu His Ala Ala
                900                 905                 910
Phe Leu Gln Ala Tyr Arg Ser Ala Leu Pro Glu Glu Ala Leu Glu Glu
```

|  |  | 915 |  |  | 920 |  |  | 925 |  |  |
|--|--|--|--|--|--|--|--|--|--|--|

Ala Gly Trp Thr Arg His Met Ala Glu Val Ala Ala Glu His Leu His
          930                     935                     940

Arg Glu Glu Arg Pro Ala Arg Lys Arg Ile His Glu Arg Trp Gln Ala
945                     950                     955                     960

Lys Ala Gly Lys Ala Pro Thr Pro Thr Pro Thr Ser Gly Pro Ala Gly
              965                     970                     975

Cys Gln Val Leu Trp Gly Val Asn Gln Trp Asn Thr Gly Phe Thr Ala
          980                     985                     990

Asn Val Thr Val Lys Asn Thr Ser Ser Ala Pro Val Asp Gly Trp Thr
          995                   1000                   1005

Leu Thr Phe Ser Phe Pro Ser Gly Gln Gln Val Thr Gln Ala Trp
         1010                   1015                   1020

Ser Ser Thr Val Thr Gln Ser Gly Ser Ala Val Thr Val Arg Asn
         1025                   1030                   1035

Ala Pro Trp Asn Gly Ser Ile Pro Ala Gly Gly Thr Ala Gln Phe
         1040                   1045                   1050

Gly Phe Asn Gly Ser His Thr Gly Thr Asn Ala Ala Pro Thr Ala
         1055                   1060                   1065

Phe Ser Leu Asn Gly Thr Pro Cys Thr Val Gly
         1070                   1075

```
<210> SEQ ID NO 4
<211> LENGTH: 2895
<212> TYPE: DNA
<213> ORGANISM: Thermus thermophilus
<300> PUBLICATION INFORMATION:
<308> DATABASE ACCESSION NUMBER: NCBI/AQOS01000019
<309> DATABASE ENTRY DATE: 2013-05-24
<313> RELEVANT RESIDUES IN SEQ ID NO: (38394)..(41288)

<400> SEQUENCE: 4
```

| | | | | |
|--|--|--|--|--|
| atggacccccc | tctggtacaa | ggacgcggtg | atctaccagc | tccacgtccg | ctccttcttt | 60 |
| gacgccaaca | acgacggcta | cggggacttt | gagggcctga | ggcggaagct | tccctacctg | 120 |
| gaggagctcg | gggtcaacac | cctctggctc | atgcccttct | tccagtcccc | cttgagggac | 180 |
| gacgggtacg | atatctccga | ctactaccag | atcctccccg | tccacgggac | cctggaggac | 240 |
| ttcaagcgct | tcctggacga | ggcccacggc | cggggggatga | aggtgatcat | tgagctcgtc | 300 |
| ctgaaccaca | cctccattga | ccacccttgg | ttccaggagg | cgaggaagcc | gaatagcccc | 360 |
| atgcggggact | ggtacgtgtg | gagcgacacc | ccggagaagt | acaagggggt | ccgggtcatc | 420 |
| ttcaaggact | ttgaaacctc | caactggacc | tttgaccccg | tggccaaggc | ctactactgg | 480 |
| caccgcttct | actggcacca | gcccgacctc | aactgggaca | ccccgaggt | ggagaaggcc | 540 |
| atccaccagg | tcatgttctt | ctgggccgac | ctggggggtgg | acggcttccg | cctggacgcc | 600 |
| atcccctacc | tctacgagcg | ggaggggacc | tcctgcgaga | acctccccga | gaccattgag | 660 |
| gcggtgaagc | gcctgaggaa | ggccctggag | gagcgctacg | ccccgggaa | gatcctcctc | 720 |
| gccgaggcca | acatgtggcc | ggaggagacc | ctcccctact | cggggacgg | gacggggtc | 780 |
| cacatggcct | acaacttccc | cctgatgccc | cggatcttca | tggccctaaa | gcggaggac | 840 |
| cgggggccca | ttgaaaccat | gctcaaggag | acggagggga | tccccgaaac | cgcccagtgg | 900 |
| gccctcttcc | tccgcaacca | cgacgagctc | accctggaga | aggtcacgga | ggaggagcgg | 960 |
| gagttcatgt | acgaggccta | cgcccccgac | cccaagttcc | gcatcaacct | ggggatccgc | 1020 |
| cgccgcctca | tgcccctcct | cggggggcgac | cgcaggcggt | acgagctcct | caccgccctc | 1080 |

```
ctcctcaccc taaagggcac gcccatcgtc tactacgggg acgagatcgg catgggggac    1140
aaccccttcc tcggggaccg gaacggggtc aggaccccca tgcagtggtc ccaagaccgc    1200
aacgccggct tctcccgcgc ccctaccac gccctcttcc ttcccccccgt gagcgagggg    1260 ccctacagct accacttcgt caacgtggag gcccagcggg aaaaccccca ctccctcctg    1320
agcttcaacc gccgcttcct cgccctgagg aaccagcacg ccaagatctt cggccggggg    1380
agcctcaccc ttctccccgt ggagaaccgg cgcgtcctcg cctacctgag ggagcacgag    1440
ggggagcggg tcctggtggt ggccaacctc tcccgctaca cccaggcctt tgacctcccc    1500
ttggaggcct accaaggcct cgtccccgtg agctcttct cgcagcaacc cttcccccccg    1560 gtggaggggc gctaccgcct gaccctgggc cccacggct tcgccctctt cgccctgaag    1620
cccgtggagg cggtgctcca cctcccctcc cccgactggg ccgaggagcc cgcccccgag    1680
gaggccgacc tgccccgggt ccacatgccc gggggccgg aggtcctcct ggtggacacc    1740
ctggtccacg aaaggggggcg ggaggagctc ctaaacgccc tcgcccagac cctgaaggag    1800
aagagctggc tcgccctcaa gccgcagaag gtggccctcc tggacgccct ccgcttccag    1860 aaggaccccgc ccctttacct caccctgctc cagctggaga accacaggac cctccaggtc    1920
ttcctccccc tcctctggtc cccccagagg cgggaaggcc ccggcctctt cgcccgcacc    1980
cacggccagc ccggctactt ctacgagctc tccttggacc caggcttcta ccgcctcctc    2040
ctcgcccgcc ttaaggaggg gtttgagggg cggagcctcc gggcctacta ccgcggccgc    2100
cacccgggtc ccgtgcccga ggccgtggac ctcctccggc cgggactcgc ggcggggag    2160 ggggtctggg tccagctcgg cctcgtccaa gacgggggcc tggaccgcac ggagcgggtc    2220 ctccccccgcc tggaccctccc ctgggttctc cggcccgaag ggggcctctt ctggagcgg    2280 ggcgcctcca gaagggtcct cgccctcacg ggaagcctcc ccccgggccg ccccccaggac    2340 ctcttcgccg ccctggaggt ccggctcctg gaaagccttc cccgcctccg ggggcacgcc    2400
cccgggaccc caggcctcct tcccggggcc ctgcacgaga ccgaagccct ggtccgcctc    2460
ctcggggtgc gcctcgccct cctccaccgg gcccttgggg aggtggaggg ggtggtgggg    2520 ggccacccccc tcctaggccg cggcctcggg gccttcctgg agctggaggg ggaggtgtac    2580
ctcgtggccc tggcgcgga aaagcggggc acggtggagg aggacctggc ccgcctggcc    2640
tacgacgtgg agcgggccgt gcacctcgcc ctcgaggccc tggaggcgga gctttgggcc    2700
tttgccgagg aggtggccga ccacctccac gccgccttcc tccaagccta ccgctccgcc    2760
ctccccgagg aggccctgga ggaggcgggc tggacgcggc acatggccga ggtggcggcg    2820
gagcacctcc accgggagga aaggcccgcc cgcaagcgca tccacgagcg ctggcaggcc    2880
aaggccggaa aagcc                                                    2895
```

<210> SEQ ID NO 5
<211> LENGTH: 342
<212> TYPE: DNA
<213> ORGANISM: Cellulomonas fimi
<300> PUBLICATION INFORMATION:
<308> DATABASE ACCESSION NUMBER: NCBI/M15824
<309> DATABASE ENTRY DATE: 1994-12-01
<313> RELEVANT RESIDUES IN SEQ ID NO: (1848)..(2189)

<400> SEQUENCE: 5

```
ccgacgccga ccccgacgtc cggtccggcc gggtgccagg tgctgtgggg cgtcaaccag     60
tggaacaccg gcttcaccgc gaacgtcacc gtgaagaaca cgtcctccgc tccggttgac    120
```

```
ggctggacgc tcacgttcag cttcccgtcc ggccagcagg tcacccaggc gtggagctcg      180
acggtcacgc agtccggctc ggccgtgacg gtccgcaacg ccccgtggaa cggctcgatc      240
ccggcgggcg gcaccgcgca gttcggcttc aacggctcgc acacgggcac caacgccgcg      300
ccgacggcgt tctcgctcaa cggcacgccc tgcacggtcg gc                         342

<210> SEQ ID NO 6
<211> LENGTH: 3237
<212> TYPE: DNA
<213> ORGANISM: Artificial Sequence
<220> FEATURE:
<223> OTHER INFORMATION: TrTS-CBD recombinant gene

<400> SEQUENCE: 6 atggacccccc tctggtacaa ggacgcggtg atctaccagc tccacgtccg ctccttcttt     60
gacgccaaca acgacggcta cggggacttt gagggcctga ggcggaagct tccctacctg     120
gaggagctcg gggtcaacac cctctggctc atgcccttct tccagtcccc cttgagggac     180
gacgggtacg atatctccga ctactaccag atcctccccg tccacgggac cctggaggac     240
ttcaagcgct tcctggacga ggccacggc cggggatga aggtgatcat tgagctcgtc       300
ctgaaccaca cctccattga ccaccttgg ttccaggagg cgaggaagcc gaatagcccc       360
atgcgggact ggtacgtgtg gagcgacacc ccggagaagt acaaggggt ccgggtcatc      420 ttcaaggact tgaaacctc caactggacc tttgaccccg tggccaaggc ctactactgg      480
caccgcttct actggcacca gcccgacctc aactgggaca ccccgaggt ggagaaggcc      540 atccaccagg tcatgttctt ctgggccgac ctggggtgg acggcttccg cctgacgcc       600 atcccctacc tctacgagcg ggagggggacc tcctgcgaga acctccccga gaccattgag    660
gcggtgaagc gcctgaggaa ggccctggag gagcgctacg ccccgggaa gatcctcctc      720 gccgaggcca acatgtggcc ggaggagacc ctcccctact cggggacgg ggacggggtc      780 cacatggcct acaacttccc cctgatgccc cggatcttca tggcccctaaa gcgggaggac    840 cggggggccca ttgaaaccat gctcaaggag acggaggga tccccgaaac cgcccagtgg     900
gccctcttcc tccgcaacca cgacgagctc accctggaga aggtcacgga ggaggagcgg    960
gagttcatgt acgaggccta cgccccccgac cccaagttcc gcatcaacct ggggatccgc   1020
cgccgcctca tgcccctcct cggggggcgac cgcaggcggt acgagctcct caccgccctc   1080
ctcctcaccc taaagggcac gcccatcgtc tactacgggg acgagatcgg catggggggac  1140 aacccccttcc tcgggggaccg gaacggggtc aggacccccca tgcagtggtc ccaagaccgc 1200
aacgccggct tctcccgcgc ccctaccac gccctcttcc ttccccccgt gagcgagggg    1260 cccctacagct accacttcgt caacgtggag gcccagcggg aaaaccccca ctccctcctg   1320
agcttcaacc gccgcttcct cgccctgagg aaccagcacg ccaagatctt cggccggggg    1380
agcctcaccc ttctccccgt ggagaaccgg cgcgtcctcg cctacctgag ggagcacgag    1440
ggggagcggg tcctggtggt ggccaacctc tcccgctaca cccaggcctt tgacctcccc     1500
ttggaggcct accaaggcct cgtccccgtg gagctcttct cgcagcaacc cttccccccg    1560 gtggagggc gctaccgcct gaccctgggc cccacggct cgccctcttt cgccctgaag      1620
cccgtggagg cggtgctcca cctccccctcc cccgactggg ccgaggagcc cgccccccgag   1680 gaggccgacc tgccccgggt ccacatgccc ggggggccgg aggtcctcct ggtggacacc    1740
ctggtccacg aaaggggggcg ggaggagctc ctaaacgccc tcgcccagac cctgaaggag   1800
aagagctggc tcgccctcaa gccgcagaag gtggccctcc tggacgccct ccgcttccag    1860
```

```
aaggacccgc ccctttacct caccctgctc cagctggaga accacaggac cctccaggtc    1920
ttcctccccc tcctctggtc cccccagagg cgggaaggcc ccggcctctt cgcccgcacc    1980
cacggccagc ccggctactt ctacgagctc tccttggacc caggcttcta ccgcctcctc    2040
ctcgcccgcc ttaaggaggg gtttgagggg cggagcctcc gggcctacta ccgcggccgc    2100
cacccgggtc ccgtgcccga ggccgtggac ctcctccggc cgggactcgc ggcgggggag    2160
ggggtctggg tccagctcgg cctcgtccaa gacgggggcc tggaccgcac ggagcgggtc    2220
ctcccccgcc tggacctccc ctgggttctc cggcccgaag ggggcctctt ctgggagcgg    2280
ggcgcctcca gaagggtcct cgccctcacg ggaagcctcc ccccgggccg ccccaggac    2340 ctcttcgccg ccctggaggt ccggctcctg gaaagccttc cccgcctccg ggggcacgcc    2400
cccgggaccc caggcctcct tcccggggcc ctgcacgaga ccgaagccct ggtccgcctc    2460
ctcggggtgc gcctcgccct cctccaccgg gcccttgggg aggtggaggg ggtggtgggg    2520
ggccaccccc tcctaggccg cggcctcggg gccttcctgg agctggaggg ggaggtgtac    2580
ctcgtggccc tgggcgcgga aaagcggggc acggtggagg aggacctggc ccgcctggcc    2640
tacgacgtgg agcgggccgt gcacctcgcc ctcgaggccc tggaggcgga gctttgggcc    2700
tttgccgagg aggtggccga ccacctccac gccgccttcc tccaagccta ccgctccgcc    2760
ctccccgagg aggccctgga ggaggcgggc tggacgcggc acatggccga ggtggcggcg    2820
gagcacctcc accgggagga aaggcccgcc cgcaagcgca tccacgagcg ctggcaggcc    2880
aaggccggaa aagcccccgac gccgaccccg acgtccggtc cggccgggtg ccaggtgctg    2940
tggggcgtca accagtggaa caccggcttc accgcgaacg tcaccgtgaa gaacacgtcc    3000
tccgctccgg ttgacggctg gacgctcacg ttcagcttcc cgtccggcca gcaggtcacc    3060
caggcgtgga gctcgacggt cacgcagtcc ggctcggccg tgacggtccg caacgccccg    3120
tggaacggct cgatcccggc gggcggcacc gcgcagttcg gcttcaacgg ctcgcacacg    3180
ggcaccaacg ccgcgccgac ggcgttctcg ctcaacggca cgccctgcac ggtcggc      3237
```

IMMOBILIZED THERMOSTABLE TREHALOSE SYNTHASE AND METHOD FOR PRODUCING TREHALOSE AND TREHALULOSE BY USING SAME

CROSS REFERENCE TO RELATED APPLICATION(S)

This application claims priority to and the benefit of Taiwanese Application No. 109143883, filed Dec. 11, 2020, the entirety of which is incorporated by reference herein.

BACKGROUND

Technical Field

The present disclosure relates to a thermostable trehalose synthase, and particularly to an immobilized thermostable trehalose synthase capable of converting maltose into trehalose or sucrose into trehalulose, an expression vector thereof, a preparation method thereof, and a method by using the thermostable trehalose synthase for producing trehalose and trehalulose.

Description of Related Art

Trehalose is a non-reducing disaccharide formed by two glucoses with α,α-1,1-glycosidic bonds. Trehalose widely exists in nature, e.g., in animals, plants and microorganisms, and has many important functions of physiological protection. Because of good physical and chemical properties, trehalose has been widely applied in pharmaceutical, food and cosmetics industries.

Trehalose dihydrate dried from diluted ethanol forms a colorless or white orthorhombic disphenoidal crystal, which has a sweet taste and can be used as a food additive and sweetener, and its sweetness is equivalent to 45% of sucrose. During the heating of trehalose with amino acids and proteins, Maillard browning reaction will not occur since trehalose is not a reducing sugar.

The biosynthetic pathways of trehalose are not completely the same in different organisms, and there are at least three known pathways.

As to the TPS-TPP pathway (also known as the OtsA-OtsB pathway), this trehalose biosynthesis pathway involves in converting uridine diphosphate-glucose (UDP-glucose) and glucose-6-phosphate into an intermediate product, trehalose-6-phosphate (T-6-P), by the catalysis of trehalose-6-phosphate synthase (TPS), and then hydrolysing a phosphate group of the intermediate product trehalose-6-phosphate by trehalose phosphate phosphatase (TPP) to produce trehalose. This pathway widely exists in archaea, bacteria, fungi, plants and arthropods.

As to the TreY-TreZ pathway (also known as the MTS-MTH pathway), this trehalose biosynthetic pathway involves in the catalysis of maltooligosyltrehalose synthase (TreY or MTS) and maltooligosyltrehalose trehalohydrolase (TreZ or MTH). The main process of the reaction is as follows. The first α-1,4 glycosidic bond between two glucoses on the reducing terminal of the maltooligosaccharide is converted into α-1,1 glycosidic bond by the catalysis of MTS, so as to form maltooligosyltrehalose, and then trehalose is produced by the catalysis of MTH, and the original maltooligosaccharide is converted into a new oligosaccharide in which two glucoses are lost. Further, the remaining maltooligosaccharide acts as a new substrate for the next round of reaction through the second α-1,4 glycosidic bond beside the original α-1,1 glycosidic bond. This pathway exists in archaea and bacteria.

As to the TreS pathway, this trehalose biosynthetic pathway involves in the catalysis of trehalose synthase (TreS) and maltose as the substrate of TreS, wherein maltose having α, α-1,4-glycosidic bond is converted into trehalose having α,α-1,1-glycosidic bond. This pathway only exists in bacteria, and is the only pathway involving a reversible reaction among these three trehalose synthesis pathways. That is to say, trehalose can also be converted into maltose by trehalose synthase.

The industrial processes for producing trehalose are roughly divided into extraction from microbial sources and enzymatic conversion method. Among them, obtaining trehalose from yeast extracts is not only difficult for purification, but also low-yield and high-cost, which does not meet the standard of commercial mass production, whereas the enzymatic conversion method is a way that has been applied in industry to produce trehalose, which can reduce costs and mass-produce trehalose.

However, the following problems exist in the TreS pathway for synthesizing trehalose. Firstly, because the temperature of the reaction must be increased to avoid bacterial contamination, the thermal stability of the TreS needs to be improved. Secondly, trehalose synthase leads to a side reaction of producing glucose, and such side reaction will increasingly occur with the increase of the reaction temperature, resulting in the low conversion rate of trehalose.

On the other hand, trehalulose is also a new type of sweetener, which is an isomer of sucrose, but has very different chemical and physical properties from sucrose. Trehalulose has extremely high solubility and hygroscopicity. Its solubility at room temperature is as high as 90%, and the sweetness is about 65% to 70% of sucrose. In nature, the content of trehalulose is quite low, even the highest content in honey is less than 1%. Therefore, the processes of producing trehalulose with higher purity are currently developing.

Trehalulose is generated from sucrose catalyzed by sucrose isomerase. Under the catalysis of sucrose isomerase, sucrose is isomerized to trehalulose as well as isomaltulose. At present, enzymatic catalysis is the most likely method for industrial production of trehalulose, while the ratio of trehalulose to isomaltulose isomerized from sucrose varies with the different sucrose isomerase from different microorganisms. Recent studies have reported that trehalose synthase from *Thermus thermophilus* has the function of sucrose isomerase and can isomerize sucrose to trehalulose (Huang et al. 2013). However, the use of trehalose synthase to produce trehalulose also faces the same problem in the use of trehalose synthase to produce trehalose as mentioned above.

In view of this, there is still a need to provide a new trehalose synthase in present, which adopts the TreS pathway to synthesize trehalose, so as to solve the aforementioned problems currently caused by adopting the TreS pathway to synthesize trehalose. At the same time, this new trehalose synthase can also be used to synthesize trehalulose.

SUMMARY

The present disclosure provides a thermostable trehalose synthase, an expression vector thereof, a preparation method thereof and a method of producing trehalose or trehalulose by using the same, which may convert maltose into trehalose, or convert sucrose into trehalulose effectively.

The thermostable trehalose synthase of the present disclosure comprises an amino acid sequence of a trehalose synthase domain and an amino acid sequence of a cellulose binding domain. In one of the embodiments of the present disclosure, said amino acid sequence of said cellulose binding domain is connected to a C-terminal of said amino acid sequence of said trehalose synthase domain. In one of the embodiments of the present disclosure, said thermostable trehalose synthase is immobilized on cellulose (e.g., microcrystalline cellulose or regenerated amorphous cellulose), presenting as an immobilized thermostable trehalose synthase. In other embodiments, said thermostable trehalose synthase is immobilized on regenerated amorphous cellulose.

The recombinant expression vector encoding the above-mentioned thermostable trehalose synthase in the present disclosure comprises a nucleotide sequence for encoding trehalose synthase domain and a nucleotide sequence for encoding cellulose binding domain. In one of the embodiments of the present disclosure, said nucleotide sequence for encoding cellulose binding domain is connected to a 3'-terminal of said nucleotide sequence for encoding trehalose synthase domain.

The present disclosure also provides a method of preparing a thermostable trehalose synthase, comprising: providing the above-mentioned recombinant expression vector; introducing said recombinant expression vector into a host to form a transformant; culturing said transformant in a medium under conditions sufficient to express the thermostable trehalose synthase from said transformant; and collecting the thermostable trehalose synthase from said medium. In one of the embodiments of the present disclosure, said preparation method further comprises attaching said thermostable trehalose synthase to cellulose, thereby forming an immobilized thermostable trehalose synthase.

In one of the embodiments of the present disclosure, the amino acid sequence of the trehalose synthase domain and the nucleotide sequence for encoding trehalose synthase domain are derived from Thermus thermophilus. In one of the embodiments of the present disclosure, the amino acid sequence of the cellulose binding domain and the nucleotide sequence for encoding cellulose binding domain are derived from *Cellulomonas fimi*.

In one of the embodiments of the present disclosure, the amino acid sequence of the trehalose synthase domain may have at least 90% (e.g., 91%, 92%, 93%, 94%, 95%, 96%, 97%, 98%, 99% or 100%) sequence identity to SEQ ID NO: 1, and have the same activity as SEQ ID NO: 1; for example, said amino acid sequence may have the activity of trehalose synthase. In other embodiments, the nucleotide sequence for encoding trehalose synthase domain may have at least 90% (e.g., 91%, 92%, 93%, 94%, 95%, 96%, 97%, 98%, 99% or 100%) sequence identity to SEQ ID NO: 4, and have the same activity as SEQ ID NO: 4; for example, said nucleotide sequence may express a protein having the activity of trehalose synthase. In one of the embodiments of the present disclosure, the sequence represented by SEQ ID NO: 4 is a nucleotide sequence of position 38,394 to position 41,288 of NCBI Accession No. AQOS01000019, having a total of 2,895 base pairs, while the sequence represented by SEQ ID NO: 1 is the amino acid sequence of NCBI Accession No. WP_024119343.

In one of the embodiments of the present disclosure, the amino acid sequence of the cellulose binding domain may have at least 90% (e.g., 91%, 92%, 93%, 94%, 95%, 96%, 97%, 98%, 99% or 100%) sequence identity to SEQ ID NO: 2, and have the same activity as SEQ ID NO: 2; for example, said amino acid sequence may bind to cellulose. In other embodiments, the nucleotide sequence for encoding cellulose binding domain may have at least 90% (e.g., 91%, 92%, 93%, 94%, 95%, 96%, 97%, 98%, 99% or 100%) sequence identity to SEQ ID NO: 5, and have the same activity as SEQ ID NO: 5; for example, said nucleotide sequence may express a protein capable of binding to cellulose. In one of the embodiments of the present disclosure, the sequence represented by SEQ ID NO: 5 is a nucleotide sequence of position 1,848 to position 2,189 of NCBI Accession No. M15824, having a total of 342 base pairs, while the sequence represented by SEQ ID NO: 2 is an amino acid sequence of position 371 to position 484 of NCBI Accession No. AAA56791.

In one of the embodiments of the present disclosure, the amino acid sequence of the thermostable trehalose synthase may have at least 90% (e.g., 91%, 92%, 93%, 94%, 95%, 96%, 97%, 98%, 99% or 100%) sequence identity to SEQ ID NO: 3, and have the same activity as SEQ ID NO: 3; for example, it may also be used for producing trehalose or trehalulose. In other embodiments, the expression vector for encoding thermostable trehalose synthase comprises a nucleotide sequence having at least 90% (e.g., 91%, 92%, 93%, 94%, 95%, 96%, 97%, 98%, 99% or 100%) sequence identity to SEQ ID NO: 6, and said nucleotide sequence has the same activity as SEQ ID NO: 6; for example, it may also express thermostable trehalose synthase.

In one of the embodiments of the present disclosure, in addition to the nucleotide sequence for encoding trehalose synthase domain and the nucleotide sequence for encoding cellulose binding domain, the recombinant expression vector may further comprise at least one selected from the group consisting of a marker gene sequence, a reporter gene sequence, an antibiotic resistance gene sequence, a cleavage site sequence of restriction enzyme, a polyadenylation site sequence, an enhancer sequence, a terminator sequence and a regulatory sequence. In other embodiments, the recombinant expression vector may be prepared by introducing the aforementioned nucleotide sequence for encoding trehalose synthase domain and the aforementioned nucleotide sequence for encoding cellulose binding domain into a conventional vector in the art. The types of conventional vectors suitable for preparing the recombinant expression vector of the present disclosure are not particularly limited, and the vectors known in the art for expressing large amounts of proteins may be used, such as pET-20b(+), pBR322, pUC18, pBluescript II SK(+), pKK223-3, pUB110, pTP4, pC194, pHV14, YRp7, YEp7, pBS7, λgt.λC, λgt.λB, ρ11, ψ1, and ψ105.

In one of the embodiments of the present disclosure, the types of host suitable for incorporating with an expression vector to form a transformant are not particularly limited, and the host commonly used in the art may be used, such as the microorganism belonging to the *Escherichia, Klebsiella, Erwinia, Serratia, Providencia, Corynebacterium* or *Brevibacterium*. In addition, in the preparation method of the present disclosure, the processes for collecting the thermostable trehalose synthase in the medium are not particularly limited; for example, the trehalose synthase expressed by the cultured transformant may be collected by centrifugation, filtration, concentration, salting out, dialysis, precipitation for separation, ion exchange chromatography, gel filtration chromatography, hydrophobic chromatography, affinity chromatography, gel electrophoresis and/or isoelectric electrophoretic analysis.

In addition to the aforementioned thermostable trehalose synthase and the preparation method thereof, the present disclosure also provides a method for producing trehalose by the thermostable trehalose synthase, which comprises mixing maltose with the thermostable trehalose synthetase of the present disclosure, thereby converting said maltose into trehalose. In addition, the present disclosure further provides a method for producing trehalulose by the heat-stable trehalose synthase, which comprises mixing sucrose with the thermostable trehalose synthase of the present disclosure, thereby converting said sucrose into trehalulose.

In one of the embodiments of the present disclosure, for the purpose of effectively synthesizing trehalose and trehalulose, said thermostable trehalose synthetase is immobilized on a support (e.g., cellulose and dietary fiber), thereby presenting as an immobilized thermostable trehalose synthase. In the present disclosure, the trehalose synthase may be immobilized on the support by the immobilization method commonly used in the art, such as solid adsorption method, embedding method, cross-linking method, and the like. In other embodiments, the immobilized thermostable trehalose synthase is immobilized on the support by solid adsorption method.

The thermostable trehalose synthase of the present disclosure may be immobilized through the cellulose binding domain of the thermostable trehalose synthase during the reaction, and thus the thermostable trehalose synthase may be easily separated from reactants or products for reuse, thereby being conducive to the industrial production of trehalose and trehalulose. In the present disclosure, the immobilized trehalose synthase exhibits superior reusability.

As mentioned above, the present disclosure provides an immobilized thermostable trehalose synthase and a preparation method thereof, wherein the prepared immobilized thermostable trehalose synthase comprises not only trehalose synthase domain but also cellulose binding domain. Through the cellulose binding domain, the trehalose synthetase may bind to non-water soluble support, such that the enzyme is confined to a certain space, leading to the advantages such as increasing the reuse rate and stability of the enzyme, easily separating the enzyme from the product, and continuously operating the reaction. Therefore, the catalytic efficiency of the enzyme may be further improved, so as to increase the economic benefits in producing trehalose and trehalulose.

BRIEF DESCRIPTIONS OF THE DRAWINGS

FIG. 1 is a schematic diagram of a recombinant expression vector according to one of the embodiments of the present disclosure. TtTS: trehalose synthase domain gene; CBD: cellulose binding domain gene; NdeI, SalI: cleavage sites of restriction enzymes; Ap: ampicillin resistance gene; His-tag: polyhistidine-tag.

FIG. 2 shows the results of evaluating the recombinant enzyme immobilized on microcrystalline cellulose according to one of the embodiments of the present disclosure. M: protein marker; 1: the soluble fraction of cell lysate; 2: the fraction not attached to the cellulose; 3 to 5: the supernatants from the first to third washings; 6: the fraction attached to the cellulose; TtTS-CBD: the recombinant enzyme of trehalose synthase domain and cellulose binding domain.

Figure 5:
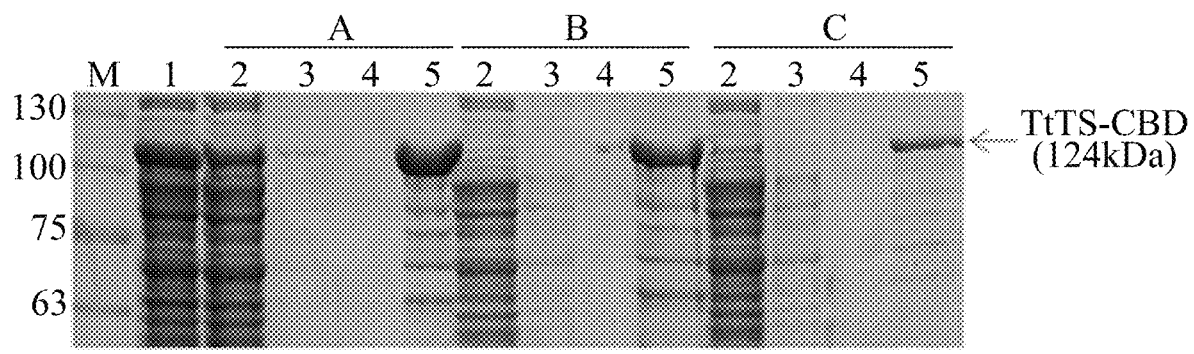

FIG. 5 shows the results of adsorbing the recombinant enzyme by regenerated amorphous cellulose according to one of the embodiments of the present disclosure. M: protein marker; A: 10 mg microcrystalline cellulose; B: 10 mg regenerated amorphous cellulose; C: 100 mg microcrystalline cellulose; 1: the soluble fraction of the cell extract; 2: the fraction not attached to the cellulose; 3, 4: the supernatants from the first and second washings; 5: the fraction attached to the cellulose; TtTS-CBD: the recombinant enzyme of trehalose synthase domain and cellulose binding domain.

Figure 6:
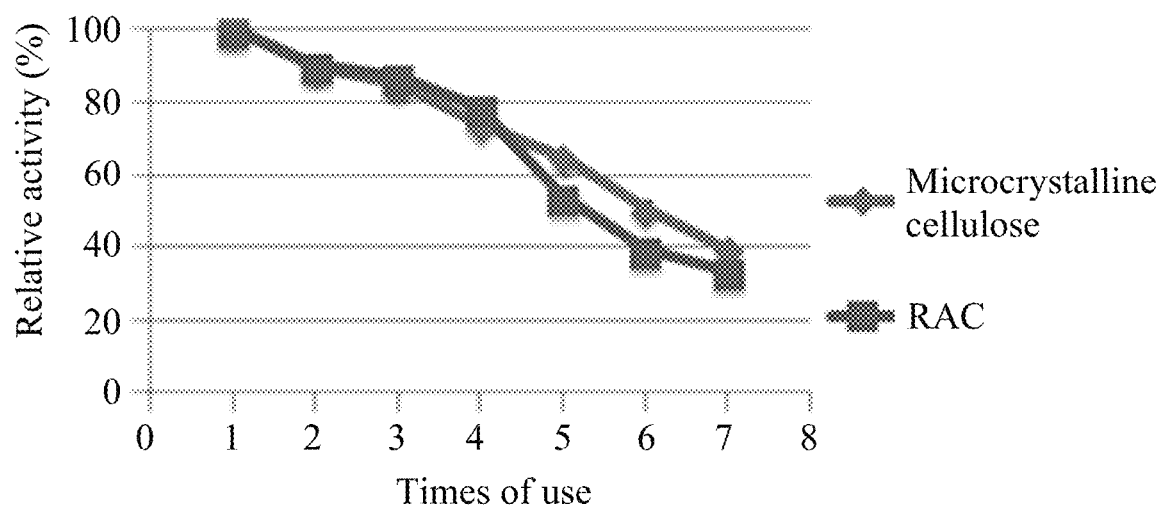

FIG. 6 shows the results of evaluating of the relative activity of the recombinant enzyme immobilized on microcrystalline cellulose or regenerated amorphous cellulose (RAC) when being repeatedly used according to one of the embodiments of the present disclosure.

Figure 7:
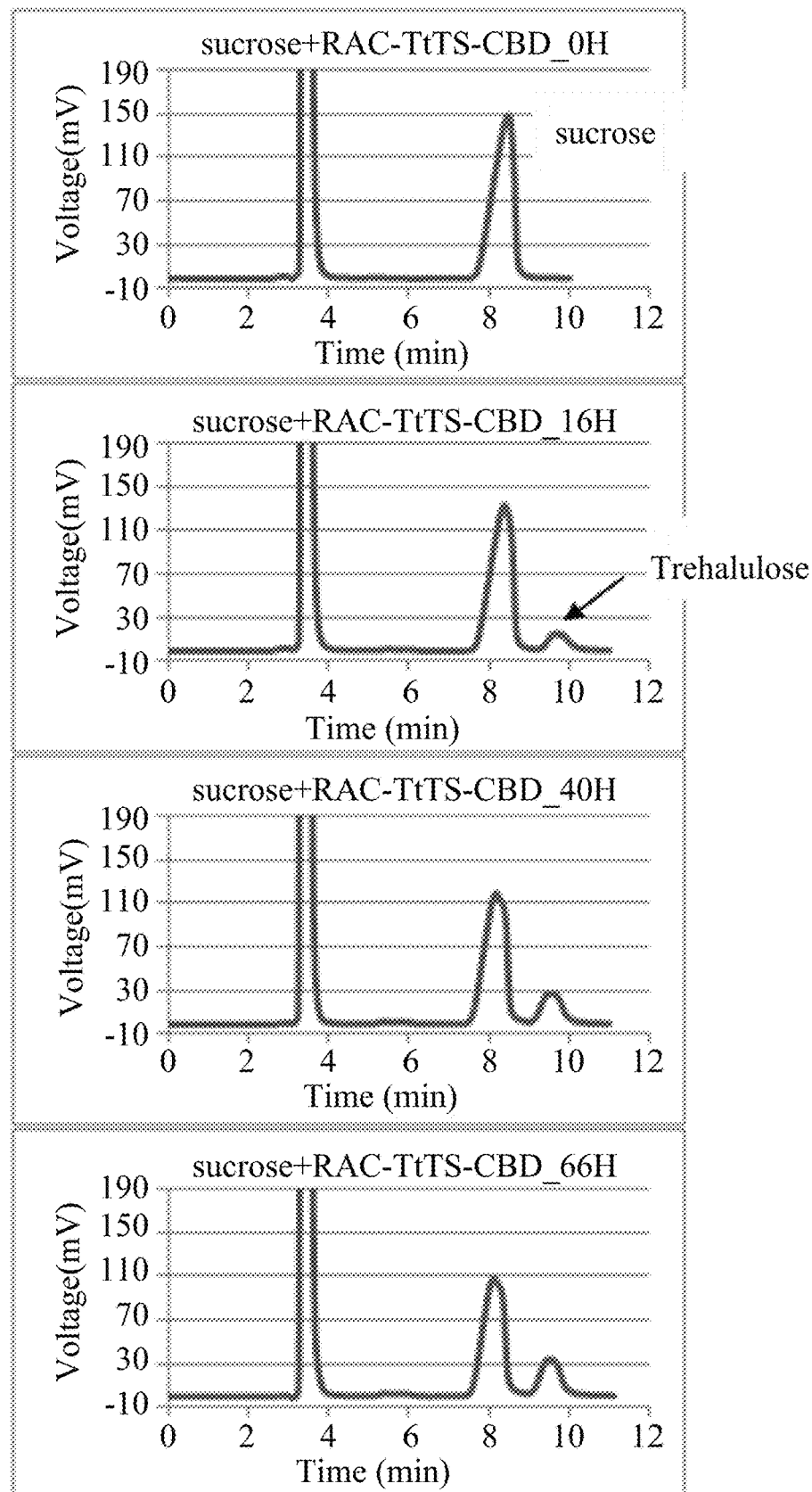

FIG. 7 shows the result of converting sucrose by the regenerated amorphous cellulose-immobilized recombinant enzyme according to one of the embodiments of the present disclosure, in which the reaction time are 0, 16, 40, and 66 hours (represented by 0H, 16H, 40H, and 66H, respectively). RAC: regenerated amorphous cellulose; TtTS-CBD: the recombinant enzyme of trehalose synthase domain and cellulose binding domain.

DETAILED DESCRIPTION OF THE EMBODIMENTS

The following aspects of embodiments are used to illustrate the technical contents of the present disclosure. A person having ordinary skill in the art can easily understand the advantages and effects after reading the present disclosure. In addition, all ranges and values herein are inclusive and combinable. Any value or point falling within the range described herein, such as any integer, can be used as the minimum or maximum value to derive the lower range.

Unless otherwise stated in the context, the singular forms "a/an" and "said" used in the specification and the appended claims include a plurality of individuals, and the term "or" includes the meaning of "and/or."

The present disclosure provides a thermostable trehalose synthase, which comprises an amino acid sequence of a trehalose synthase domain and a amino acid sequence of a cellulose binding domain. The present disclosure also provides a recombinant expression vector for encoding said thermostable trehalose synthase and a method for producing trehalose or trehalulose by using said thermostable trehalose synthase.

In one of the embodiments of the present disclosure, the trehalose synthase domain of the thermostable trehalose synthase may directly convert maltose into trehalose by, for example, converting the α,α-1,4-glycosidic bond of maltose into α,α-1,1-bond. In addition, said trehalose synthase domain may also directly convert sucrose into trehalulose.

In one of the embodiments of the present disclosure, the amino acid sequence of the trehalose synthase domain and the nucleotide sequence for encoding trehalose synthase domain have at least 90% (e.g., 91%, 92%, 93%, 94%, 95%, 96%, 97%, 98%, 99% or 100%) sequence identity to SEQ ID NO: 1 and SEQ ID NO: 4, respectively.

As used herein, the term "sequence identity" means the percentage that the amino acid or nucleotide residues of a candidate protein or nucleic acid fragment are completely identical to the amino acid or nucleotide residue of a reference protein or nucleic acid fragment. When performing the above comparison, said candidate protein or nucleic acid fragment may be aligned, and the gaps may be introduced as necessary, so as to form the highest sequence identity between the two sequences. The amino acid residue where is conservative substitution is regarded as different residue, and the nucleotide residues which are degenerated codons are also regarded as different residues, when calculating the identity; for example, it is considered that there is a different residue U or C between the codons AAU and AAC that both encode asparagine.

It should be understood that compared to the amino acid or nucleotide sequence of a reference protein or nucleic acid fragment in the present disclosure, amino acid or nucleotide sequence of a candidate protein or nucleic acid fragment, which is modified (e.g., deleted, substituted or added) at least a part in the sequence, is also within the scope of the present disclosure, as long as the resulting candidate protein or nucleic acid fragment has substantially the same biological activity as the amino acid or nucleotide of the reference protein or nucleic acid fragment. This results from the codon degeneracy. In other words, a person having ordinary skill in the art can understand that the amino acid sequence of the trehalose synthase domain and the nucleotide sequence for encoding trehalose synthase domain may have variation, as long as the structure of the active region and the important amino acids in the amino acid sequence of the trehalose synthase domain are not changed, and the effect of converting maltose into trehalose can be achieved.

Therefore, the nucleotide sequence for encoding trehalose synthase domain provided in the present disclosure may be any nucleotide sequence having the nucleotide sequence of SEQ ID NO: 4 or having at least 90% sequence identity to SEQ ID NO: 4, as long as the protein encoded by said nucleotide sequence can exhibit the activity of the trehalose synthase domain. Similarly, the trehalose synthase domain provided in the present disclosure may be any protein having the amino acid sequence of SEQ ID NO: 1 or homologous to SEQ ID NO: 1, as long as said protein can substantially exhibit the activity of the trehalose synthase domain.

As used herein, the term "cellulose-binding domain (CBD)" refers to a protein or functional fragment thereof that has a high affinity for cellulose. Cellulose binding domain is discontinuous domains on scaffoldin of cellulosome, wherein the cellulosome is an enzyme complex for cellulose degradation, and is mainly composed of two functional domains, i.e., catalytic domain and cellulose binding domain.

In the thermostable trehalose synthase of the present disclosure, the cellulose binding domain may be the cellulose binding domain derived from different species. At present, there are more than 200 kinds of cellulose binding domain, and the dominated cellulose binding domain may be found in polysaccharide-degrading enzyme. In addition, cellulose binding domain may also be found in cellulase, hemicellulase, mannanase, xylanase and some non-hydrolyzing proteins. The known cellulose binding domains can be divided into about 39 kinds depending on their amino acid sequences, in which the 6 most common cellulose binding domains are CBD1, CBD2, CBD3, CBD4, CBD5 and CBD9. CBD1 is a cellulose binding domain produced by fungi; CBD2 to CBD5 are cellulose binding domains mainly produced by bacteria; and CBD9 is only found in bacterial xylanase (Ouyang et al., 2008).

In the thermostable trehalose synthase of the present disclosure, the cellulose binding domain is derived from *Cellulomonas fimi*. The cellulose binding domain of *Cellulomonas fimi* has excellent binding ability to microcrystalline cellulose. When cotton fabric is used as a support, the amount of cotton fabric binding to cellulose binding domain can increase with exposure of microcrystalline cellulose during boiling-out; however, the present disclosure is not limited thereto.

In addition, a person having ordinary skill in the art can understand that the amino acid sequence of the cellulose binding domain and the nucleotide sequence for encoding cellulose binding domain may have variation, as long as the structure of the active region and the important amino acids in the amino acid sequence of the cellulose binding domain are not changed, and the purpose of immobilizing the thermostable trehalose synthase on cellulose can be achieved. Therefore, the nucleotide sequence for encoding cellulose binding domain provided in the present disclosure may be any nucleotide sequence having the nucleotide sequence of SEQ ID NO: 5 or having at least 90% (e.g., 91%, 92%, 93%, 94%, 95%, 96%, 97%, 98%, 99% or 100%) sequence identity to SEQ ID NO: 5, as long as the protein encoded by said nucleotide sequence can exhibit the activity of the cellulose binding domain. Similarly, the cellulose binding domain of the present disclosure may be any protein having the amino acid sequence of SEQ ID NO: 2 or homologous to SEQ ID NO: 2, as long as said protein can substantially exhibit the activity of the cellulose binding domain.

In the thermostable trehalose synthase of the present disclosure, the amino acid sequence of the cellulose binding domain is located at C-terminal, and the amino acid sequence of the trehalose synthase domain is located at N-terminal. That is to say, the amino acid sequence of the cellulose binding domain is connected to the C-terminal of the amino acid sequence of the trehalose synthase domain, and there may be an additional amino acid fragment as a linker therebetween, which would not affect enzyme activity. For example, in the thermostable trehalose synthetase of the present disclosure, the amino acid sequence of the cellulose binding domain is connected to the C-terminal of the amino acid sequence of the trehalose synthase domain through a linker, which is a fragment composed of the first to sixth amino acids at the N-terminal of SEQ ID NO: 2.

In the recombinant expression vector for encoding thermostable trehalose synthase provided in the present disclosure, the nucleotide sequence for encoding cellulose binding domain is connected to the 3'-terminal of the nucleotide sequence for encoding trehalose synthase domain, and there may be an additional nucleotide fragment as a linker therebetween, which would not affect the enzyme expression.

As used herein, the term "recombinant" refers to the artificial combination of two separate sequence fragments. Generally, the term "recombinant" means that a nucleic acid, protein or microorganism contains genetic material derived from multiple different sources, or is encoded by the genetic material derived from multiple different sources, such as two or more kinds of organisms belonging to different strains or species.

According to the embodiments of the present disclosure, the thermostable trehalose synthase of the present disclosure is a fusion protein formed by trehalose synthase domain and cellulose binding domain. The thermostable trehalose synthase of the present disclosure may be immobilized on the cellulose through the cellulose binding domain to form an immobilized thermostable trehalose synthase during the reaction, and thus it may be easily separated from reactants or products and may be reused, thereby being conducive to the industrial production of trehalose.

When the immobilized thermostable trehalose synthase of the present disclosure is used to produce trehalose, the reaction is a single catalytic process and has the advantages such as the preparation process being simple and the reaction process to be easily controlled. Moreover, the immobilized thermostable trehalose synthase of the present disclosure is specific to the substrate, which only works on maltose, but not other sugar such as glucose, maltooligosaccharide and lactose. In addition, the immobilized thermostable trehalose synthase is more conducive to the industrial production of trehalose, because using maltose as substrate may lower the raw material cost.

The trehalose synthetase provided in the present disclosure has two different converting functions. Under the general conditions of biochemical reaction, said enzyme may convert maltose into trehalose and may also convert sucrose into trehalulose. Both of trehalose and trehalulose may be used in the fields such as food industry, beverages and functional foods, cosmetics, pharmaceutical and biological products.

Many examples have been used to illustrate the present disclosure. The examples below should not be taken as a limit to the scope of the present disclosure.

EXAMPLES

Example 1

Preparation of the Recombinant Expression Vector

Figure 1:
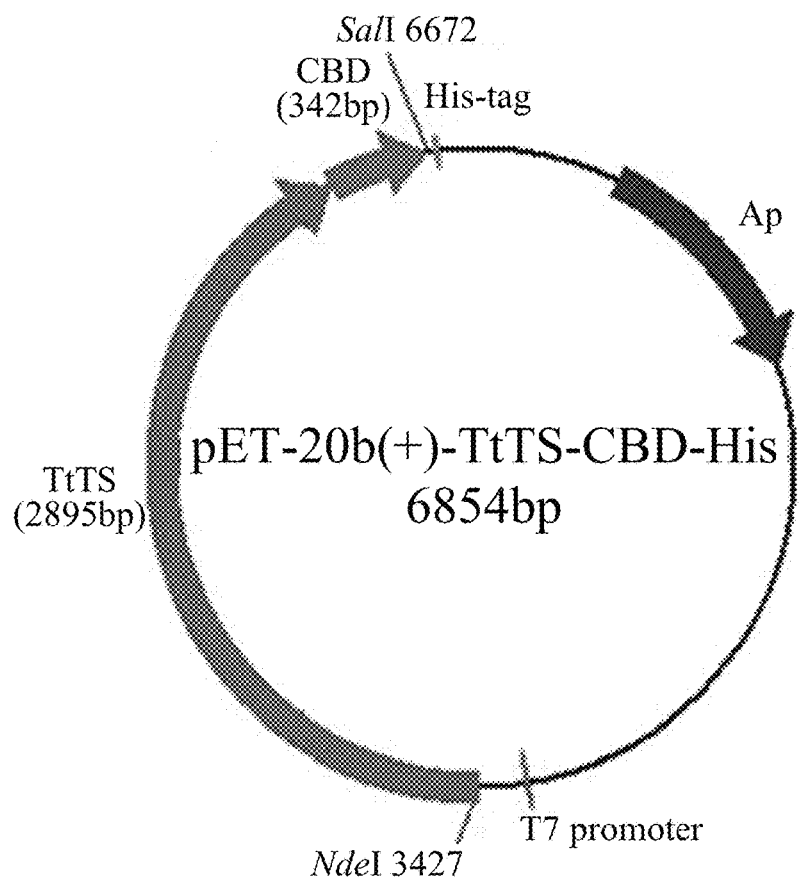

According to the nucleotide sequence of the trehalose synthase domain (SEQ ID NO: 4) of *Thermus thermophiles* ATCC 33923 of position 38,394 to position 41,288 of NCBI Accession No. AQOS01000019 and the nucleotide sequence of the cellulose binding domain (SEQ ID NO: 5) of *Cellulomonas fimi* of position 1,848 to position 2,189 of NCBI Accession No. M15824, a fragment which was the combination of the two sequences and has 3,237 base pairs (SEQ ID NO: 6) was synthesized by full-length gene synthesis. Further, said fragment was cut with restriction enzymes NdeI and SalI, and then ligated with a plasmid pET-20b(+) which was also cut with the same enzymes, so as to obtain a recombinant vector pET-20b(+)-TtTS-CBD. The schematic diagram of pET-20b(+)-TtTS-CBD was shown in FIG. 1, in which TtTS referred to trehalose synthase domain, and CBD referred to cellulose binding domain.

Afterwards, the recombinant vector was introduced into a commercially available *E. coli* strain DH5α, and then cultured in an LB medium containing ampicillin with the final concentration of 100 μg/mL. Further, a strain successfully transformed with the recombinant vector was selected.

Example 2

Expression of the Thermostable Trehalose Synthase

The pET-20b(+)-TtTS-CBD selected in Example 1 was introduced into another strain *E. coli* Tuner (DE3) pLysS to obtain *E. coli* Tuner (DE3) pLysS pET-20b(+)-TtTS-CBD transformant.

Said transformant was cultured in an LB medium containing 100 μg/mL ampicillin and 34 μg/mL chloramphenicol overnight. Subsequently, the cultured transformant was diluted with LB medium containing 100 μg/mL ampicillin, 34 μg/mL chloramphenicol and 0.5 mM isopropyl β-d-1-thiogalactopyranoside (IPTG) in a dilution ratio of 1:50. After incubating at 20° C. for 24 hours, the cells were collected by centrifugation, and then suspended in 20 mM sodium phosphate buffer (pH 7.0) in a volume ratio of 1/10. Furhter, the cells were dissolved/lysed by ultrasonic vibration, and subjected to centrifugation at 10,000×g for 10 minutes, so as to obtain a supernatant (i.e., crude cell extract). Said supernatant contained the recombinant protein having the trehalose synthase domain and the cellulose binding domain (i.e., the thermostable trehalose synthase of the present disclosure).

Example 3

Immobilization of the Recombinant Protein on Microcrystalline Cellulose

First, 20 mg of microcrystalline cellulose (Type 50, Sigma, St. Louis, Mo.) was added to 10 mL of the crude cell extract prepared in Example 2, and slowly stirred for 1 hour at room temperature. Afterwards, the suspension was centrifuged (8,000×g, 5 minutes, 25° C.), and the supernatant was removed. The cellulose precipitate was washed three times, in which the first washing was performed by a solution containing 2 mL 1 M NaCl and 20 mM sodium phosphate (pH 7), while the other two washings were performed by a solution of 20 mM sodium phosphate (pH 7). Each washing was performed under slowly stirring at room temperature for 30 minutes. After each washing, the suspension was centrifuged (8,000×g, 5 minutes, 25° C.), and the supernatant was removed. After the last washing, the cellulose precipitate was resuspended in 2.5 mL of a solution of 20 mM sodium phosphate (pH 7). The suspension was transferred to a clean test tube and further centrifuged, and then the supernatant was removed. Finally, the fraction attached to the cellulose, the fraction not attached to the cellulose, the washing solutions and the crude cell extract obtained initially were detected by SDS-PAGE analysis.

Figure 2:
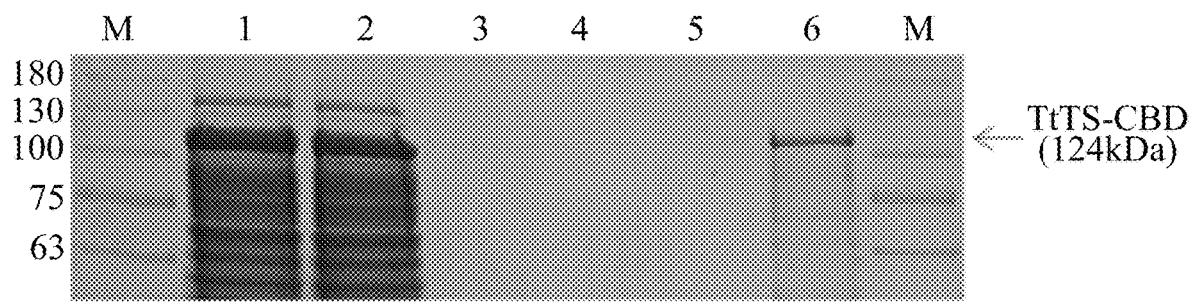

The results were shown in FIG. 2, wherein M referred to the pre-dyed protein marker; 1 referred to the soluble fraction of the cell lysate (i.e., the crude cell extract obtained initially); 2 referred to the fraction not attached to the cellulose; 3 to 5 referred to the supernatants obtained from the first to third washings, respectively; and 6 referred to the fraction attached to the cellulose. These results showed that the recombinant TtTS-CBD fusion protein may be adsorbed on cellulose.

Example 4

Evaluation of the Trehalose Conversion Rate of the Immobilized Enzyme

With reference to the method described in Example 3, 1 mL crude cell extracts adsorbed on 100 mg of microcrystalline cellulose (i.e., the immobilized enzyme) was prepared, and suspended in 1 mL of a solution of 20 mM sodium phosphate (pH 7). Then, 250 μL of the suspension containing the immobilized enzyme and 750 μL of 40% maltose (dissolved in 20 mM sodium phosphate (pH 7)) were mixed in a rotating mixer and reacted at 60° C. for 24 hours. After the reaction, the contents of maltose, glucose and trehalose in the reaction solution were analyzed by high performance liquid chromatography (HPLC), and then the trehalose conversion rate and the glucose hydrolysis rate were calculated.

Figure 3:
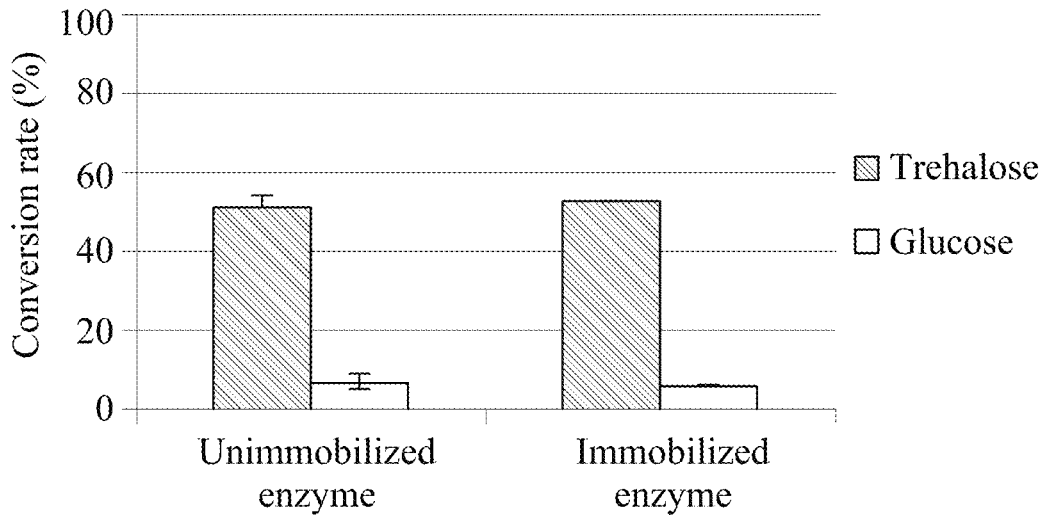
FIG. 3 shows the results of evaluating the conversion rate of the unimmobilized recombinant enzyme and the microcrystalline cellulose-immobilized recombinant enzyme according to one of the embodiments of the present disclosure.

The results were shown in FIG. 3, indicating that under the conditions of using a reaction solution containing 25 mg of the immobilized enzyme on microcrystalline cellulose and maltose with a final concentration of 30%, and having pH 7.0 and a total volume of 1 mL, followed by reaction in a rotary mixer at 60° C. for 24 hours, the trehalose conversion rate of the immobilized enzyme was 53.61%, and the glucose hydrolysis rate was 8.69%.

In addition, in order to compare the conversion efficiency of the immobilized enzyme and the unimmobilized enzyme, the unimmobilized TtTS-CBD recombinant protein prepared in Example 2 and maltose were reacted according to the aforementioned reaction conditions. The results showed that the trehalose conversion rate of the unimmobilized enzyme was 52.35%, and the glucose hydrolysis rate was 9.47%. It can be seen that the catalytic activity of the immobilized enzyme was slightly increased in comparison with the unimmobilized enzyme, indicating that the immobilization of the recombinant enzyme would not negatively affect the enzyme activity.

Example 5

Evaluation of the Efficiency of the Reused Immobilized Enzyme

The immobilized enzyme was prepared by the method described in Example 4, and then 25 mg of the immobilized enzyme on microcrystalline cellulose and maltose (dissolved in 20 mM sodium phosphate (pH 7)) were evenly mixed, so as to obtain a reaction solution having a total volume of 1 mL, and the final concentration of maltose being 30%. The reaction solution was then reacted in a rotary mixer at 60° C. for 24 hours, followed by centrifuging at 10,000×g for 5 minutes. The supernatant was collected and stored in a refrigerator at −20° C. for the subsequent HPLC analysis. In addition, after the centrifugation, the precipitated immobilized enzyme was further mixed and completely suspended in 1 mL of 30% maltose, and reacted in a rotary mixer at 60° C. for 24 hours. The aforementioned enzyme reaction was repeated 7 times.

Figure 4:
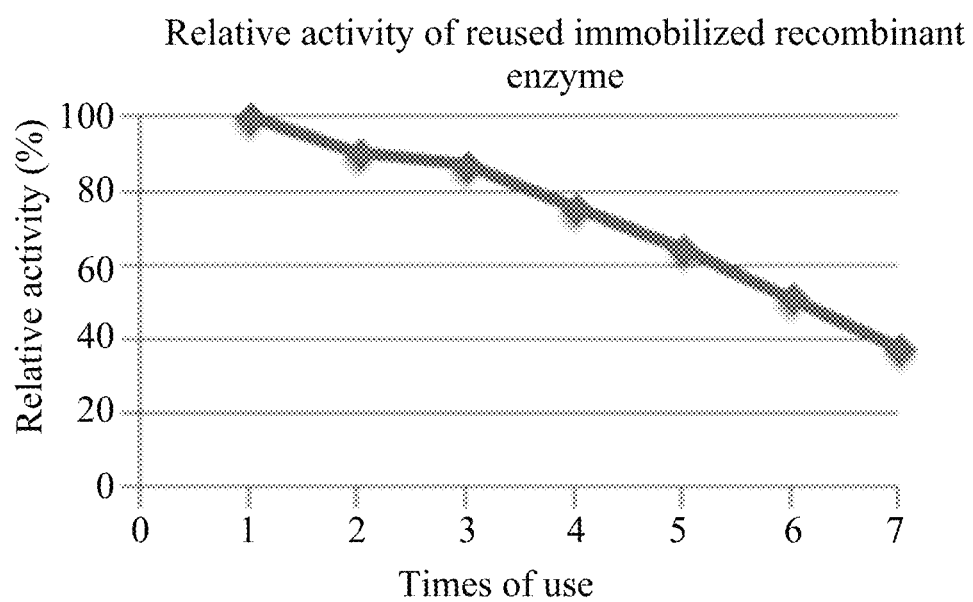
FIG. 4 shows the results of evaluating the relative activity of the recombinant enzyme immobilized on microcrystalline cellulose according to one of the embodiments of the present disclosure when being repeatedly used.

The results were shown in FIG. 4 and Table 1 below, indicating that even though the immobilized enzyme had been reused for six times, 51% of the trehalose conversion rate could be maintained in comparison to the conversion rate of the first use.

slurry. Further, 10 mL of cold 86% H3PO4 (commercially available grade, 85%) was slowly added to the slurry under vigorous stirring, and the final concentration of phosphoric acid was calculated as 83.2%. The cellulose mixture became transparent within a few minutes. At the same time, the cellulose mixture was placed in an ice bath and occasionally stirred for 1 hour.

Next, about 40 mL of ice water was partially added to the cellulose mixture by 10 mL each time, and the mixture was stirred vigorously after each addition of ice water, so as to obtain a white misty precipitate. The obtained cellulose was centrifuged at about 10,000×g at 4° C. for 20 minutes, and the obtained precipitate was suspended in ice water, and then centrifuged to remove phosphoric acid from the supernatant. The foregoing processes were repeated four times in total. Afterwards, the cellulose precipitate was neutralized and suspended in about 0.5 mL of 2 M Na2CO3 and 40 mL of ice distilled water. After centrifugation, the precipitate was washed twice with distilled water, or the pH value thereof reached 5 to 7. Finally, the resulting regenerated amorphous cellulose was suspended in 30 mL of distilled water for later use.

Example 7

Immobilization of the Recombinant Protein on Regenerated Amorphous Cellulose

With reference to the method described in Example 3, the regenerated amorphous cellulose prepared in Example 6 was subjected to the step of adsorbing the recombinant protein, and analyzed by SDS-PAGE to evaluate the adsorption amount of the amorphous cellulose.

The results were shown in FIG. 5, in which M referred to pre-dyed protein marker; A referred to the group of 10 mg microcrystalline cellulose adsorbing 1 mL of the crude cell extract; B referred to the group of 10 mg regenerated amorphous cellulose adsorbing 1 mL of the crude cell extract; C referred to the group of 100 mg microcrystalline cellulose adsorbing 1 mL of the crude cell extract; 1 referred to the soluble fraction of the crude cell extract; 2 referred to the fraction not attached to the cellulose; 3 and 4 referred to the supernatants obtained from washings; and 5 referred to

TABLE 1

Trehalose conversion rate of the reused immobilized enzyme

| | Times of use | | | | | | |
|---|---|---|---|---|---|---|---|
| | 1 | 2 | 3 | 4 | 5 | 6 | 7 |
| Glucose (%) | 6.19 | 5.21 | 4.87 | 3.84 | 3.02 | 2.34 | 1.70 |
| Maltose (%) | 40.42 | 46.51 | 48.58 | 55.95 | 62.66 | 70.35 | 78.06 |
| Trehalose (%) | 53.39 | 48.28 | 46.55 | 40.21 | 34.32 | 27.30 | 20.24 |
| Relative conversion rate of trehalose (%) | 100.0 | 90.42 | 87.19 | 75.32 | 64.28 | 51.13 | 37.91 |

Example 6

Preparation of the Regenerated Amorphous Cellulose

Regenerated amorphous cellulose (RAC) was prepared from microcrystalline cellulose, and the process was briefly described as follows.

Firstly, about 0.2 g of microcrystalline cellulose (brand name: Avicel) and 0.6 mL of distilled water were added into a 50 mL centrifuge tube to form a cellulose suspension the fraction attached to the cellulose. By comparing A-2, B-2 and C-2 in FIG. 5, it was found that the thinner bands of TtTS-CBD referred to the more amount of TtTS-CBD adsorbed by microcrystalline cellulose or regenerated amorphous cellulose in the crude cell extract. The thinnest TtTS-CBD band of B-2 indicated that the efficiency of regenerated amorphous cellulose in adsorbing TtTS-CBD was higher than that of microcrystalline cellulose in adsorbing TtTS-CBD.

Subsequently, as to the suspension comprising the immobilized enzyme on regenerated amorphous cellulose and the suspension comprising the immobilized enzyme on microcrystalline cellulose, the TtTS-CBD adsorption amounts of the two kinds of cellulose therein were analyzed by protein assay. The results showed that the adsorption capacity of regenerated amorphous cellulose was about 150 times higher than that of microcrystalline cellulose, and the reason might be that the surface area of regenerated amorphous cellulose was higher than that of microcrystalline cellulose.

Example 8

Evaluation of the Efficiency of the Reused Immobilized Enzyme on Regenerated Amorphous Cellulose For evaluating the efficiency of the immobilized enzyme on regenerated amorphous cellulose in comparison with the immobilized enzyme on microcrystalline cellulose, the two kinds of immobilized enzymes with about equal amounts of the absorbed recombinant protein TtTS-CBD were independtly mixed with maltose (dissolved in 20 mM sodium phosphate (pH 7)), so as to obtain a reaction solution having a total volume of 1 mL and the final concentration of maltose being 30%. The reaction solution was then reacted in a rotary mixer at 60° C. for 24 hours followed by centrifuging at 11,000 r.p.m. for 5 minutes. The supernatant was collected and stored in a refrigerator at −20° C. for the subsequent HPLC analysis. In addition, after the centrifugation, the precipitated immobilized enzyme was further mixed and completely suspended in 1 mL of 30% maltose, and reacted in a rotary mixer at 60° C. for 24 hours. The aforementioned enzyme reaction was repeated 7 times.

The results were shown in FIG. 6 and Table 2 below, indicating that even though the immobilized enzyme had been reused for six times, 51% of the trehalose conversion rate could be maintained in comparison to the conversion rate of the first use.

The results were shown in FIG. 6 and Table 2 below, indicating that even though the TtTS-CBD recombinant protein immobilized on microcrystalline cellulose (C) had been reused for six times, it still retained 50% relative activity. As for the TtTS-CBD recombinant protein immobilized on regenerated amorphous cellulose, it still retained 50% relative activity even though it had been reused for five times.

TABLE 2

Trehalose conversion rate of the reused immobilized enzyme on regenerated amorphous cellulose

| | | Times of use | | | | | | |
|---|---|---|---|---|---|---|---|---|
| | | 1 | 2 | 3 | 4 | 5 | 6 | 7 |
| Trehalose (%) | RAC | 54.39 | 49.04 | 47.30 | 42.79 | 29.13 | 21.46 | 18.25 |
| | C | 54.02 | 48.45 | 46.01 | 39.98 | 35.15 | 27.30 | 21.39 |
| Relative conversion rate (%) | RAC | 100.00 | 90.17 | 86.98 | 78.68 | 53.56 | 39.45 | 33.56 |
| | C | 100.00 | 89.70 | 85.18 | 74.02 | 65.07 | 50.54 | 39.59 |

Example 9

Conversion of Sucrose into Trehalulose by Using the Immobilized Enzyme on Regenerated Amorphous Cellulose The suspension containing the immobilized enzyme on regenerated amorphous cellulose was prepared according to the method described in Example 7, and then mixed with a sucrose solution (i.e., 20 mM sodium phosphate (pH 7) in which sucrose was dissolved), so as to obtain a reaction solution containing 0.3 mg/mL of the immobilized enzyme TtTS-CBD on regenerated amorphous cellulose and 30% of the sucrose substrate. The reaction was carried out at 65° C., and the reaction time was 0, 16, 40, or 66 hours. At the end of the reaction, the enzyme reaction was terminated by heating at 99° C. for 10 minutes.

Afterwards, the resulting sample was filtered with a 4 mm PVDF 0.22 μm syringe filter (MS, SFPVDF004022N), and analyzed by HPLC equipped with an analytical column SUPELCOSIL LC-$NH_2$4.6×250 (mm). The instrument setting conditions were a flow rate of 1.0 mL/min, column temperature and detector temperature being 40° C., moving phase being acetonitrile: dd$H_2$O=85:15 v/v%. The results were shown in FIG. 7. After 16 hours of reaction, trehalulose production was detectable. It could be seen that the immobilized recombinant protein TtTS-CBD might also be used to produce trehalulose.

The above-mentioned embodiments are used to exemplify the principles and effects of the present disclosure, but not limit thereto. Those of ordinary skill in the art can modify the above-mentioned embodiments without departing from the scope of the present disclosure. Therefore, the scope of the present disclosure should be set forth in the appended claims.

What is claimed is:

1. A thermostable trehalose synthase, consisting essentially of:
   an amino acid sequence of a trehalose synthase domain derived from *Thermus thermophilus*; wherein said trehalose synthase domain converts maltose into trehalose and/or converts sucrose into trehalulose; and
   an amino acid sequence of a cellulose binding domain; wherein said amino acid sequence of said cellulose binding domain has at least 90% sequence identity to SEQ ID NO: 2, and wherein said cellulose binding domain binds cellulose; wherein said amino acid sequence of said cellulose binding domain is connected to a C-terminal of said amino acid sequence of said trehalose synthase domain through a linker, and said linker consists of consecutive amino acids selected from Threonine and Proline at an N-terminal of SEQ ID NO: 2.

2. The thermostable trehalose synthase of claim 1, wherein said amino acid sequence of said cellulose binding domain is derived from *Cellulomonas fimi*.

3. The thermostable trehalose synthase of claim 1, which is immobilized on a cellulose, presenting as an immobilized thermostable trehalose synthase.

4. The thermostable trehalose synthase of claim 3, wherein said cellulose is regenerated amorphous cellulose.

5. The thermostable trehalose synthase of claim 1, wherein said amino acid sequence of said trehalose synthase domain has at least 90% sequence identity to SEQ ID NO: 1, and wherein said trehalose synthase domain converts maltose into trehalose and/or converts sucrose into trehalulose.

6. The thermostable trehalose synthase of claim 1, which has an amino acid sequence having at least 90% sequence identity to SEQ ID NO: 3, and converts maltose into trehalose and/or converts sucrose into trehalulose.

7. The method of claim 1, wherein said thermostable trehalose synthase maintains a trehalose relative conversion rate of over 50% after at least five uses.

8. An expression vector for encoding the thermostable trehalose synthase of claim 1, consisting essentially of:
   a nucleotide sequence encoding the trehalose synthase domain derived from Thermus thermophiles; wherein said encoded trehalose synthase domain converts maltose into trehalose and/or converts sucrose into trehalulose; and
   a nucleotide sequence encoding the cellulose binding domain, wherein said nucleotide sequence encoding said cellulose binding domain has at least 90% sequence identity to SEQ ID NO: 5, and said encoded cellulose binding domain binds cellulose wherein said nucleotide sequence encoding said cellulose binding domain is connected to the 3'-terminal of said nucleotide sequence encoding said trehalose synthase domain and said cellulose binding domain encodes a linkage of consecutive amino acids consisting of Threonine and Proline.

9. The expression vector of claim 8, wherein said nucleotide sequence encoding said cellulose binding domain is derived from *Cellulomonas fimi*.

10. The expression vector of claim 8, wherein said nucleotide sequence encoding said trehalose synthase domain has at least 90% sequence identity to SEQ ID NO: 4, and converts maltose into trehalose and/or converts sucrose into trehalulose.

11. The expression vector of claim 8, which has a nucleotide sequence having at least 90% sequence identity to SEQ ID NO: 6, and encodes a trehalose synthase which converts maltose into trehalose and/or converts sucrose into trehalulose.

12. A method for producing trehalose, comprising mixing maltose with the thermostable trehalose synthase according to claim 1 to convert said maltose into trehalose.

13. The method of claim 12, further comprising immobilizing the thermostable trehalose synthase on microcrystalline cellulose or regenerated amorphous cellulose to form an immobilized thermostable trehalose synthase.

14. A method for producing trehalose, comprising mixing sucrose with the thermostable trehalose synthase according to claim 1 to convert said sucrose into trehalulose.

15. The method of claim 14, further comprising immobilizing the thermostable trehalose synthase on microcrystalline cellulose or regenerated amorphous cellulose to form an immobilized thermostable trehalose synthase.

* * * * *